US00PP33391P2

(12) United States Plant Patent
Schlup et al.

(10) Patent No.: US PP33,391 P2
(45) Date of Patent: Aug. 24, 2021

(54) ***CANNABIS* PLANT NAMED 'PG 1 19 0125 0002'**

(50) Latin Name: ***Cannabis* hybrid**
Varietal Denomination: PG 1 19 0125 0002

(71) Applicant: Pure Cannabis Research AG, Zug (CH)

(72) Inventors: Yannik Schlup, Zurich (CH); Gavin George, Zurich (CH); Michael Ruckle, Winterberg (CH)

(73) Assignee: Pure Cannabis Research AG, Zug (CH)

( * ) Notice: Subject to any disclaimer, the term of this patent is extended or adjusted under 35 U.S.C. 154(b) by 0 days.

(21) Appl. No.: 16/873,352

(22) Filed: Mar. 26, 2020

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/00; A01H 6/28; A61K 36/185; A61K 36/00
See application file for complete search history.

(56) References Cited

PUBLICATIONS

International Code of Nomenclature for Cultivated Plants 2016 Ninth ed., 2 introductory pages, iii, iv, pp. 28-32. (Year: 2016).*

* cited by examiner

*Primary Examiner* — June Hwu
(74) *Attorney, Agent, or Firm* — Knobbe, Martens, Olson & Bear, LLP

(57) ABSTRACT

A new and distinct *Cannabis* cultivar named 'PG 1 19 0125 0002' is characterized by its dominant CBG chemotype, which is favorable for application as a medicinal product. Furthermore, it may be used for the industrial-scale extraction of CBG due to the minimal concentrations of contaminating cannabinoids which may otherwise complicate the extraction of this class of secondary metabolites.

16 Drawing Sheets

Latin name of the genus claimed: *Cannabis* Hybrid.
Variety denomination: 'PG 1 19 0125 0002'.

BACKGROUND AND SUMMARY OF THE INVENTION

A novel *Cannabis* hybrid cultivar, entitled 'PG 1 19 0125 0002' is provided. 'PG 1 19 0125 0002' is the result of a planned breeding program and originated from crosses between privately-owned cultivars. The new cultivar has been vegetatively reproduced by cloning using stem cuttings at Zeiningen, Switzerland. Vegetative clones of 'PG 1 19 0125 0002' were tested in controlled indoor growth facilities, greenhouses, and outdoors in open fields. The desired characteristics of each source cultivar are transferred by vegetative, asexual reproduction. 'PG 1 19 0125 0002' is stable and consistently true-to-type through multiple generations of vegetative reproduction.

*Cannabis* is a genus of flowering plants comprising three historically distinct subspecies based on phenotype and metabolite profiles—*Cannabis sativa, Cannabis indica*, and *Cannabis ruderalis*. However, decades of crossing and selection makes it impossible to absolutely characterize the resulting hybrid plants using phenotypic data. Most of the *Cannabis* varieties being sold for medicinal and recreational purposes contains characteristics of both *Cannabis sativa* and *Cannabis indica* subspecies. For this reason, 'PG 1 19 0125 0002', described herein, has been characterized both on the presented phenotype, as well as the genotype using a series of single nucleotide polymorphisms (SNP).

Used herein, the terms "cultivar", "variety", "clone" and "strain" are used interchangeably.

*Cannabis* plants synthesize unique terpeno-phenolic compounds in varying concentrations. High genetic variability has resulted in the vast varieties of chemotypes with distinct characteristics available today. More than 500 unique compounds including cannabinoids, terpenoids, terpenes, flavonoids, amino acids, vitamins among many others, are secreted as a sticky resin by the glandular trichomes found on the floral calyxes of female plants. Cannabinoids and terpenes are the biologically active chemicals responsible for the pharmacological and psychoactive properties of *Cannabis* when consumed by humans. They often work together synergistically in what is commonly known as the "entourage effect" and as such, small differences in composition or concentration any of these compounds can have notable effects on the physiological effect of consumed or applied *Cannabis* in or on the human body.

Cannabinoids are produced at significant concentrations in *Cannabis*. Although over a hundred cannabinoids have been identified in *Cannabis*, the major cannabinoids include, Δ9-tetrahydrocannabinol (THC), cannabidiol (CBD), cannabigerol (CBG), cannabinol (CBN), cannabichromene (CBC), cannabinodiol (CBDL), cannabicyclol (CBL), cannabivarin (CBDV), cannabigerovarin (CBGV), cannabichromevarin (CBCV), tetrahydrocannabivarin (THCV), cannabidivarin (CBDV), cannabigerol monomethyl ether (CBGM), cannabilsoin (CBE), cannabicitran (CBT), cannabinol propyl variant (CBNV), cannabitriol (CBO), tetrahydrocannabinolic acid (THCA), tetrahydrocannabivarinic acid (THCVA), cannabidiolic acid (CBDA), cannabigerolic acid (CBGA) and cannabinerolic acid. These cannabinoids are usually produced by the plant in their acid form (see suffix -A), but upon heating they become. decarboxylated.

CBGA is the precursor to CBDA and THCA. CBG is usually present at very low concentrations due to its rapid utilization by CBDA or THCA synthases. It is non-psychoactive and has been described to display analgesic, antibiotic and anti-inflammatory effects. It has further been shown to reduce blood clotting and to relieve the intraocular pressure experienced by glaucoma patients. CBG further reduces the effect of THC and is actively being studied in its acid and neutral forms in many medical conditions.

As used herein, CBG will refer to both the decarboxylated form, CBG, and CBGA. The value "Total CBG" will refer to the calculated sum of both isoforms when decarboxylated i.e. Total CBG=GBGA×87.8%+CBG. Total THC and CBD are similarly calculated but with a conversion factor of 87.7%.

Terpenes are organic molecules produced by various plants and animals. These organic compounds are responsible for the strong and distinctive smell and taste of *Cannabis*. Some of the most prominent terpenes found in *Cannabis* are myrcene, caryophyllene, and limonene, to mention a few.

The objective of the breeding program that produced 'PG 1 19 0125 0002' was to develop *Cannabis* plant varieties with unique combinations of cannabinoids and/or terpenes, while displaying a phenotype with multiple large inflorescences arranged in a naturally branched habit. The variety described herein is a result of this breeding program.

The 'PG 1 19 0125 0002' cultivar was the result of poly-cross between several hemp-type and high CBD-type *Cannabis* plants. Selected progenies were then cloned and crossed by selfing using methods known in the art. In subsequent generations, the resultant plants were screened for high total CBG production and selected based on production-relevant phenotypes. The progeny with the most stable desirable chemotype was assigned the name, 'PG 1 19 0125 0002'.

The 'PG 1 19 0125 0002' plants described herein were grown in Zeiningen, Switzerland, in nurseries, climate-controlled growth facilities, and in the field during the summer of 2019. Samples for metabolite analysis were taken from the flowers of numerous plants. Analytical measurements were made using Ultra Performance Liquid Chromatography by those skilled in the art. Plant phenotyping was performed using photography and subsequent analysis.

The 'PG 1 19 0125 0002' variety described herein is extremely low in contaminating cannabinoids such as THC and CBD allowing for easier extraction of the CBG contained in the flowers. In addition, the low THC concentration facilitates extraction in that cannabinoids can be concentrated to a higher level, during the extraction process.

'PG 1 19 0125 0002' flowers were analyzed at harvest in both indoor growth and outdoor growth environments (Table 1). The resultant cannabinoid profile highlights the uniquely high CBG, and low THC and CBD content characterizing the 'PG 1 19 0125 0002' variety. It has a cannabinoid profile in the dried mature female flowers that is dominant in CBG (>5% w/w) and displays only trace amounts of THC (<0.1% w/w) and CBD (<0.1% w/w).

'PG 1 19 0125 0002' presents with a low total terpene content. In fresh flowers the total measurable terpene content is between 0.05 and 0.07% (w/w) in the fresh flowers, and between 0.9 and 0.12% (w/w) in dried flowers. The dominant terpene found in fresh flowers is Myrcene followed by trans-Caryophyllene and Limonene (Table 2). The unique profile of the major and minor terpenes makes 'PG 1 19 0125 0002' distinguishable from other varieties, including Santhica 27 and PG_1_Pre-19_0125_0004.

TABLE 1

Cannabinoid Concentrations in 'PG 1 19 0125 0002'

| | 'PG 1 19 0125 0002' | | Santhica 27 | PG_1_Pre-19_0125_0004 |
|---|---|---|---|---|
| | Indoor Flowers | Outdoor Flowers | Outdoor Flowers | Outdoor Flowers |
| | Range of active cannabinoids (% by weight) | | | |
| TOTAL CBG | 7.2-8.105 | 5.6-9.442 | 0.4-1.4 | 11.5-15.5 |
| TOTAL THC | 0.07-0.13 | 0.053-0.13 | — | 0.45-0.75 |
| TOTAL CBD | 0-0.03 | 0.001-0.21 | 0-0.2 | 0.85-1.34 |
| CBC | 0.03-0.29 | 0.03-0.39 | — | 0-0.15 |

TABLE 2

Terpene Concentrations in 'PG 1 19 0125 0002'

| | Fresh Flowers | Dry Flowers |
|---|---|---|
| | Ranges of Terpenes (% by weight) | |
| alpha-Pinene | 0.000-0.001% | — |
| (−)-beta-Pinene | 0.001-0.001% | — |
| Myrcene | 0.028-0.031% | 0.010-0.012% |
| (R)-(+)-Limonene | 0.004-0.006% | 0.001-0.002% |
| p-Cymene | 0.00% | 0.005-0.008% |
| Linalool | 0.001-0.003% | 0.00% |
| L-Fenchone | — | 0.003-0.006% |
| (+)-Fenchol | 0.00% | — |
| (−)-Isopulegol | 0.000-0.001% | — |
| (−)-alpha-Terpineol | 0.00% | — |
| Citral Isomer 2 | 0.000-0.001% | 0.002-0.003% |
| (−)-trans-Caryophyllene | 0.007-0.009% | 0.003-0.009% |
| alpha-Humulene | 0.002-0.003% | 0.002-0.003% |
| Nerolidol Isomer 2 | 0.001-0.004% | 0.004-0.009% |
| (−)-alpha-Bisabolol | 0.003-0.004% | 0.009-0.016% |
| Phytol Isomer 2 | 0.003-0.006% | 0.037-0.060% |

The genotype of 'PG 1 19 0125 0002' was characterized using Genotyping-by-sequencing (GBS) using methods described in the art. Short-read sequencing data produced by this method were aligned to the publicly available assembled genome of cs10 (Assembly: GCF_900626175.1) to identify single nucleotide polymorphisms (SNP) and short haplotypes (HAP, a combination of linked SNPs) in 'PG 1 19 0125 0002' (Table 3 and FIG. 14).

Together these polymorphisms provide a fingerprint which can be used to differentiate 'PG 1 19 0125 0002' from all other *Cannabis* varieties.

Table 3 shows a list of single nucleotide polymorphisms (SNPs) and haplotypes (HAPs) contained within the genome of 'PG 1 19 0125 0002' compared to the publicly available reference genome of cs10 (Assembly: GCF_900626175.1). Each record shows the reference chromosome of cs10, the nucleotide position on the cs10 reference sequence, the nucleotide sequence at this position, the nucleotide sequence displayed in 'PG 1 19 0125 0002', and whether the state of the polymorphism is homozygous or heterozygous in 'PG 1 19 0125 0002'. Heterozygous loci contain one allele sequence identical to the reference nucleotide sequence and one allele of the 'PG 1 19 0125 0002' sequence.

TABLE 3

| Reference chromosome (cs10) | Position in reference sequence | Reference nucleotide sequence | 'PG 1 19 0125 0002' Sequence | State |
|---|---|---|---|---|
| NC_044370.1 | 2085232 | AA | AT | homozygous |
| NC_044370.1 | 4838286 | CGT | CGC | homozygous |
| NC_044370.1 | 36467493 | C | T | homozygous |
| NC_044370.1 | 11271773 | CA | CG | homozygous |
| NC_044370.1 | 11271954 | CAG | AAG | homozygous |
| NC_044370.1 | 13526608 | CAA | CTG | homozygous |
| NC_044379.1 | 57862779 | C | T | homozygous |
| NC_044379.1 | 57863241 | GGTAC | AAAGC | homozygous |
| NC_044379.1 | 57915145 | TT | TC | homozygous |
| NC_044379.1 | 57954931 | C | G | homozygous |
| NC_044379.1 | 58169058 | GTG | CAA | homozygous |
| NC_044379.1 | 58292575 | ATCCAA | GTCCCA | homozygous |
| NC_044379.1 | 58292927 | T | C | homozygous |
| NC_044379.1 | 26744250 | G | T | homozygous |
| NC_044379.1 | 61946066 | A | G | homozygous |
| NC_044379.1 | 62821655 | G | C | homozygous |
| NC_044371.1 | 3483276 | ACG | ACA | homozygous |
| NC_044371.1 | 66149411 | T | A | homozygous |
| NC_044371.1 | 75422669 | TGA | CGT | homozygous |
| NC_044371.1 | 75974152 | GCC | GTC | homozygous |
| NC_044371.1 | 81582801 | TT | CT | homozygous |
| NC_044371.1 | 82218848 | GAG | AGT | homozygous |
| NC_044371.1 | 82483522 | GC | AA | homozygous |
| NC_044371.1 | 30915413 | A | G | homozygous |
| NC_044372.1 | 2710529 | T | C | homozygous |
| NC_044372.1 | 2710755 | TG | CG | homozygous |
| NC_044372.1 | 80252454 | G | T | homozygous |
| NC_044372.1 | 1890501 | T | C | homozygous |
| NC_044373.1 | 7589246 | CA | GA | homozygous |
| NC_044373.1 | 16326218 | AA | GG | homozygous |
| NC_044373.1 | 18857773 | T | G | homozygous |
| NC_044373.1 | 26968201 | TCC | TCT | homozygous |
| NC_044373.1 | 29630917 | G | A | homozygous |
| NC_044373.1 | 44999598 | C | T | homozygous |
| NC_044373.1 | 46220665 | CT | TG | homozygous |
| NC_044373.1 | 65997446 | C | T | homozygous |
| NC_044373.1 | 65997630 | A | G | homozygous |
| NC_044373.1 | 78468284 | G | C | homozygous |
| NC_044373.1 | 90475592 | AAGG | AAAA | homozygous |
| NC_044373.1 | 91302456 | ATAA | CTAA | homozygous |
| NC_044374.1 | 721191 | GC | CC | homozygous |
| NC_044374.1 | 2380328 | T | A | homozygous |
| NC_044374.1 | 7842585 | C | T | homozygous |
| NC_044374.1 | 46733863 | T | A | homozygous |
| NC_044374.1 | 81289150 | C | T | homozygous |
| NC_044374.1 | 87026417 | CT | GT | homozygous |
| NC_044374.1 | 53042056 | C | G | homozygous |
| NC_044374.1 | 75148552 | C | T | homozygous |
| NC_044374.1 | 79606305 | GCG | CTA | homozygous |
| NC_044374.1 | 40728787 | A | G | homozygous |
| NC_044374.1 | 81665769 | ATGC | ATGT | homozygous |
| NC_044375.1 | 93189088 | A | G | homozygous |
| NC_044375.1 | 5028137 | CGT | TGT | homozygous |
| NC_044375.1 | 5229457 | TAT | CAT | homozygous |
| NC_044375.1 | 92418831 | AGCC | AACC | homozygous |
| NC_044375.1 | 36259780 | GA | GC | homozygous |
| NC_044375.1 | 27969778 | GA | GG | homozygous |
| NC_044375.1 | 47220146 | C | G | homozygous |
| NC_044376.1 | 3765575 | CCT | TTT | homozygous |
| NC_044376.1 | 4038278 | AGG | CAG | homozygous |
| NC_044376.1 | 35656963 | TGG | CGA | homozygous |
| NC_044376.1 | 41113525 | GACG | GTCG | homozygous |
| NC_044376.1 | 49690671 | A | G | homozygous |
| NC_044376.1 | 57526518 | TC | GC | homozygous |
| NC_044376.1 | 61093783 | TA | AG | homozygous |
| NC_044377.1 | 491424 | CTG | CAT | homozygous |
| NC_044377.1 | 570205 | TCT | AAT | homozygous |
| NC_044377.1 | 22400517 | A | G | homozygous |
| NC_044377.1 | 29225173 | T | A | homozygous |
| NC_044377.1 | 36155194 | AGG | CGG | homozygous |
| NC_044377.1 | 44377730 | GG | CG | homozygous |
| NC_044377.1 | 53006255 | A | T | homozygous |
| NC_044377.1 | 61322716 | AGC | AAA | homozygous |
| NC_044377.1 | 72446888 | G | A | homozygous |

TABLE 3-continued

| Reference chromosome (cs10) | Position in reference sequence | Reference nucleotide sequence | 'PG 1 19 0125 0002' Sequence | State |
|---|---|---|---|---|
| NC_044377.1 | 78287396 | TTGTC | GTGTC | homozygous |
| NC_044378.1 | 108801 | TT | TC | homozygous |
| NC_044378.1 | 459898 | TATA | TTCA | homozygous |
| NC_044378.1 | 19944962 | GC | AG | homozygous |
| NC_044378.1 | 23972788 | CT | CA | homozygous |
| NC_044378.1 | 29436763 | CCCCCC | ACCCTT | homozygous |
| NC_044378.1 | 46687062 | GGCG | GGCA | homozygous |
| NC_044378.1 | 53550861 | CAGG | TGGA | homozygous |
| NC_044378.1 | 63538044 | GT | GA | homozygous |
| NC_044378.1 | 66753962 | GGGT | GAGT | homozygous |
| NC_044370.1 | 72116963 | CC | TT | heterozygous |
| NC_044370.1 | 104558715 | AC | CC | heterozygous |
| NC_044371.1 | 42597265 | TT | TC | heterozygous |
| NC_044372.1 | 35317415 | CTC | GTC | heterozygous |
| NC_044372.1 | 63982910 | GGCG | GCCG | heterozygous |
| NC_044375.1 | 69785254 | GCG | TTA | heterozygous |
| NC_044379.1 | 12989226 | CT | TC | heterozygous |
| NC_044379.1 | 41567327 | CAAAC | ATTGC | heterozygous |

End of Table 2.

Based on the chemotype, past research shows that 'PG 1 19 0125 0002' may have medicinal applications in the treatment of certain cancer types, pain, infection and inflammation, Glaucoma and cardiovascular disease.

THE CLONING PROCESS FOR VEGETATIVE OR ASEXUAL REPRODUCTION

Asexual or vegetative propagation methods (also known as cloning) are well-known to those skilled in the art. 'PG 1 19 0125 0002' is cloned according the following method: Coco peat plugs are soaked in pH adjusted water and kept warm. Cuttings measuring 10-12 cm are taken 3 nodes from the branch distal meristem and trimmed of lower leaves. The cuttings are dipped in water and a commercial rooting agent and inserted into the warmed plugs. Trays are kept in continuous light conditions and high humidity for 7 to 15 days until rooted. Rooted plants may be transferred directly into the field for outdoor growth or used for indoor growth. The initial asexual propagation took place in Zeiningen, Switzerland.

It was observed that all of the desired characteristics of each clone are transferred by vegetative reproduction in a consistent and uniform fashion. The characteristics of 'PG 1 19 0125 0002' are stable and the variety remains true-to-type through multiple generations of vegetative reproduction.

GROWTH OF PLANTS IN INDOOR ENVIRONMENTS

Rooted clones are transferred to two-gallon pots containing growth medium consisting of a mixture of soil, peat and pearlite in a ratio of 3:3:1. Plants are grown in an indoor growth hall under completely supplied artificial high-pressure sodium (HPS) lighting (E-Papillon, 1000W, 400V). The air in the room was circulated with a fan and the humidity was kept constant at 45-55%. Commercial fertilizer is applied at a dose of 70-80% of the amount recommended by the manufacturer (Plagron, NL). The plants are grown for 10 days with a light intensity between 700-800 μmol $m^{-2}$ $s^{-1}$, 18 h light/6 h dark day-night photoperiod with a 24-25° C. day/18° C. night temperature. The photoperiod is then changed to a 12 h light/12 h dark day-night cycle and the light intensity increased by 100 μmol $m^{-2}$ $s^{-1}$ per day for 7 days, at 25° C. day/23° C. night temperatures. During the following 60 days the light intensity is adjusted to 1400-1500 μmol $m^{-2}$ $s^{-1}$ with a 12 h light/12 h dark day-night photoperiod and a 24-25° C. day/18° C. night temperature. After a total of 84-91 days of growth after cloning, the flowers are harvested.

GROWTH OF PLANTS OUTDOORS

Field growth of 'PG 1 19 0125 0002' was performed in Zeiningen, Switzerland during the summer of 2019. The weather during the year of 2019 is presented in FIG. 13. Rooted clones were planted in the field on the 1st of July 2019. Mature flowers were then collected during the first two weeks of October.

BRIEF DESCRIPTION OF THE DRAWINGS

FIG. 13A Annual global radiation, FIG. 13B sunshine and FIG. 13C temperatures in Möhlin, the closest weather station to the breeding site of 'PG 1 19 0125 0002'. Data range shown is from November 2018 to November 2019. Data courtesy of the Swiss Federal Office of Meteorology and Climatology.

DESCRIPTION OF THE NEW VARIETY

Figure 1:
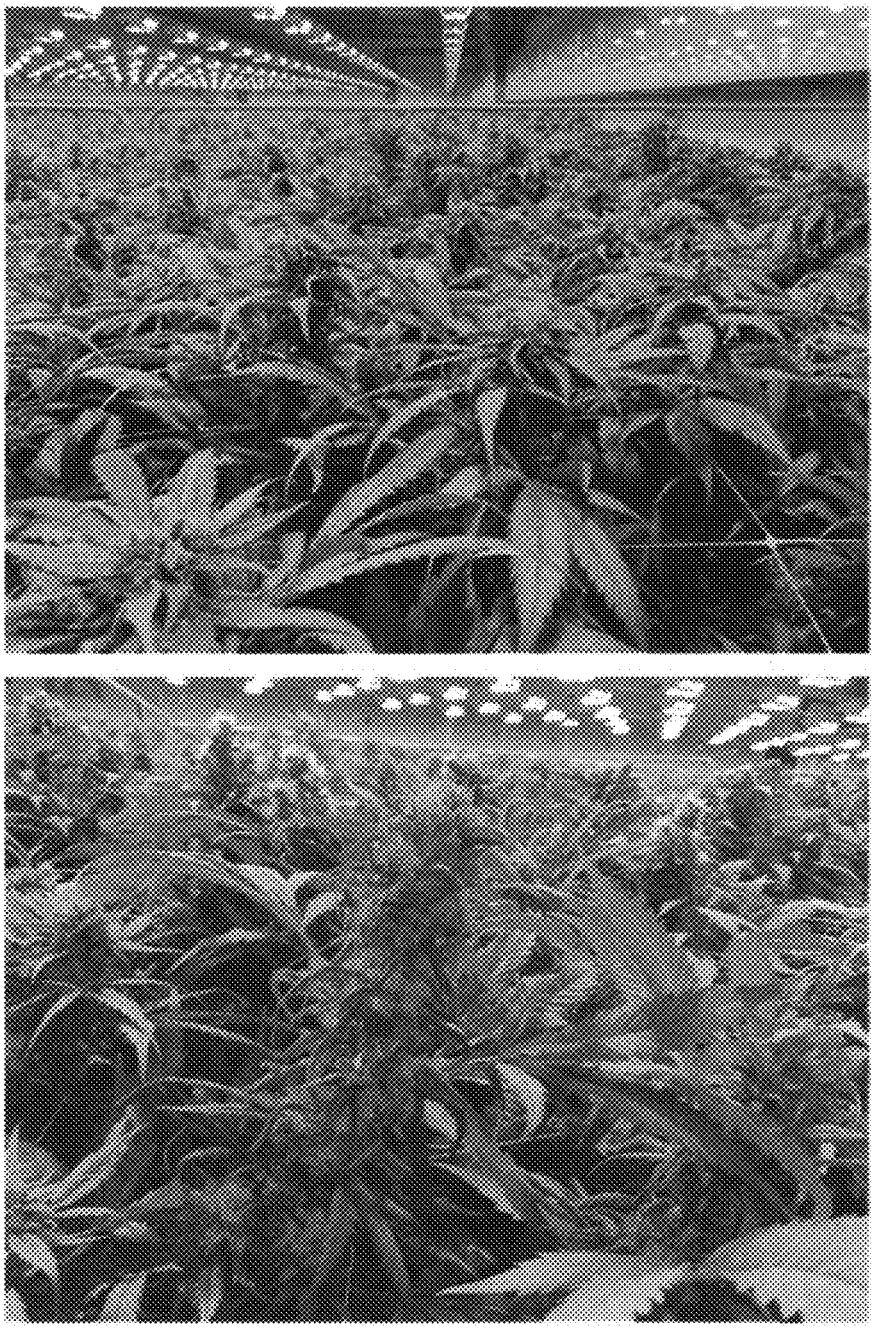
FIG. 1: Representative pictures of the 'PG 1 19 0125 0002' flower phenotype when grown under indoor conditions (10 days before harvest).
Figure 2:
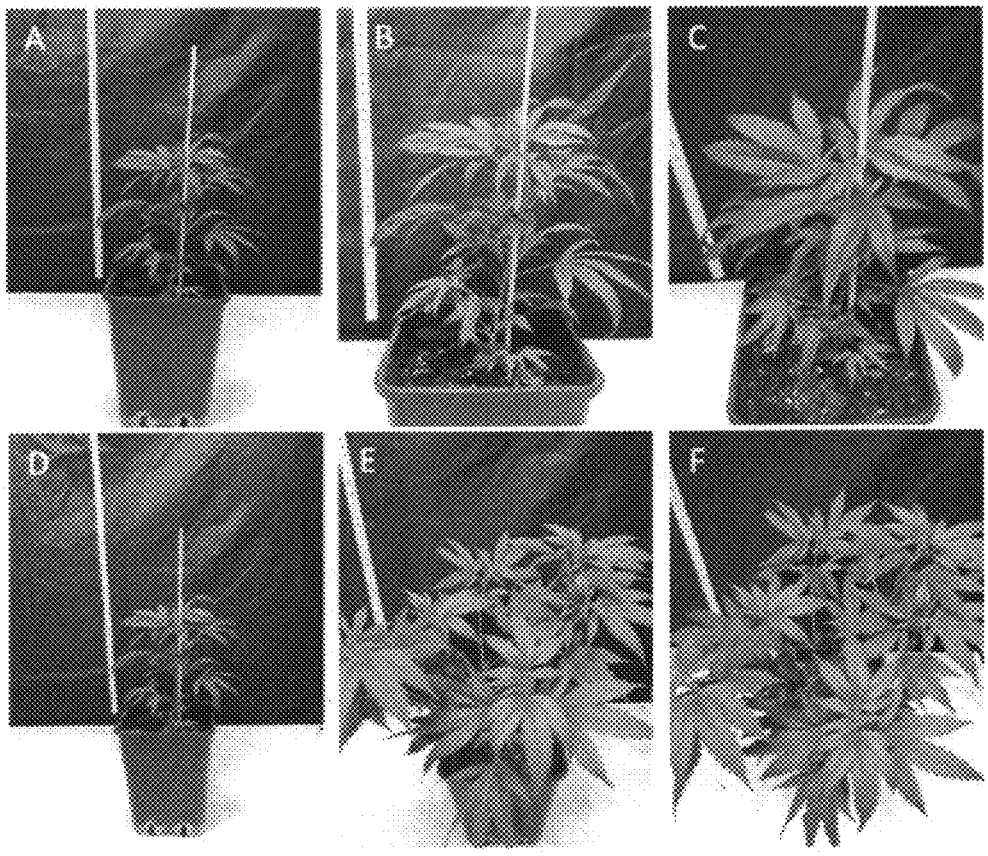
FIG. 2: 'PG 1 19 0125 0002', indoor grown, growth pattern during vegetative growth phase. A-C and D-F represent individual plants photographed from increasing inclination for descriptive purposes. Both plants were photographed 28-35 days after cloning. Ruler for scale with cm markings.
Figure 3:
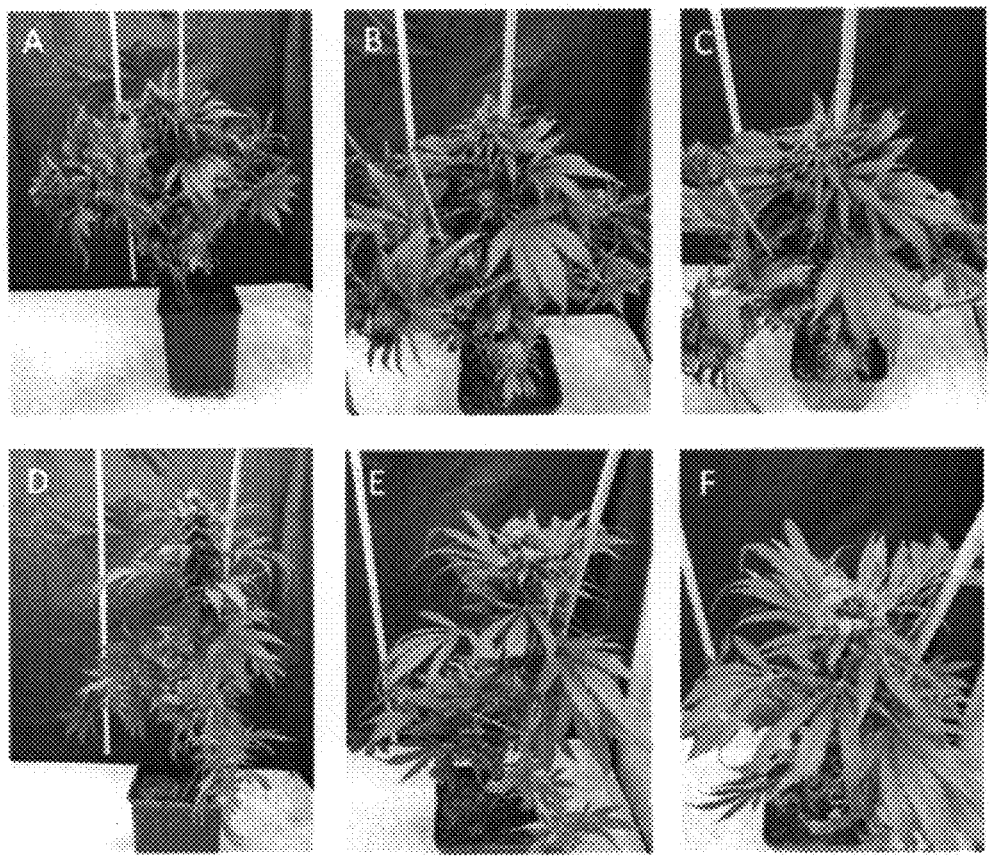
FIG. 3: 'PG 1 19 0125 0002', indoor grown, growth pattern during flowering. A-C and D-F represent individual plants photographed from increasing inclination for descriptive purposes. Both plants were photographed 1-3 days prior to harvest. Ruler for scale with cm markings.
Figure 4:
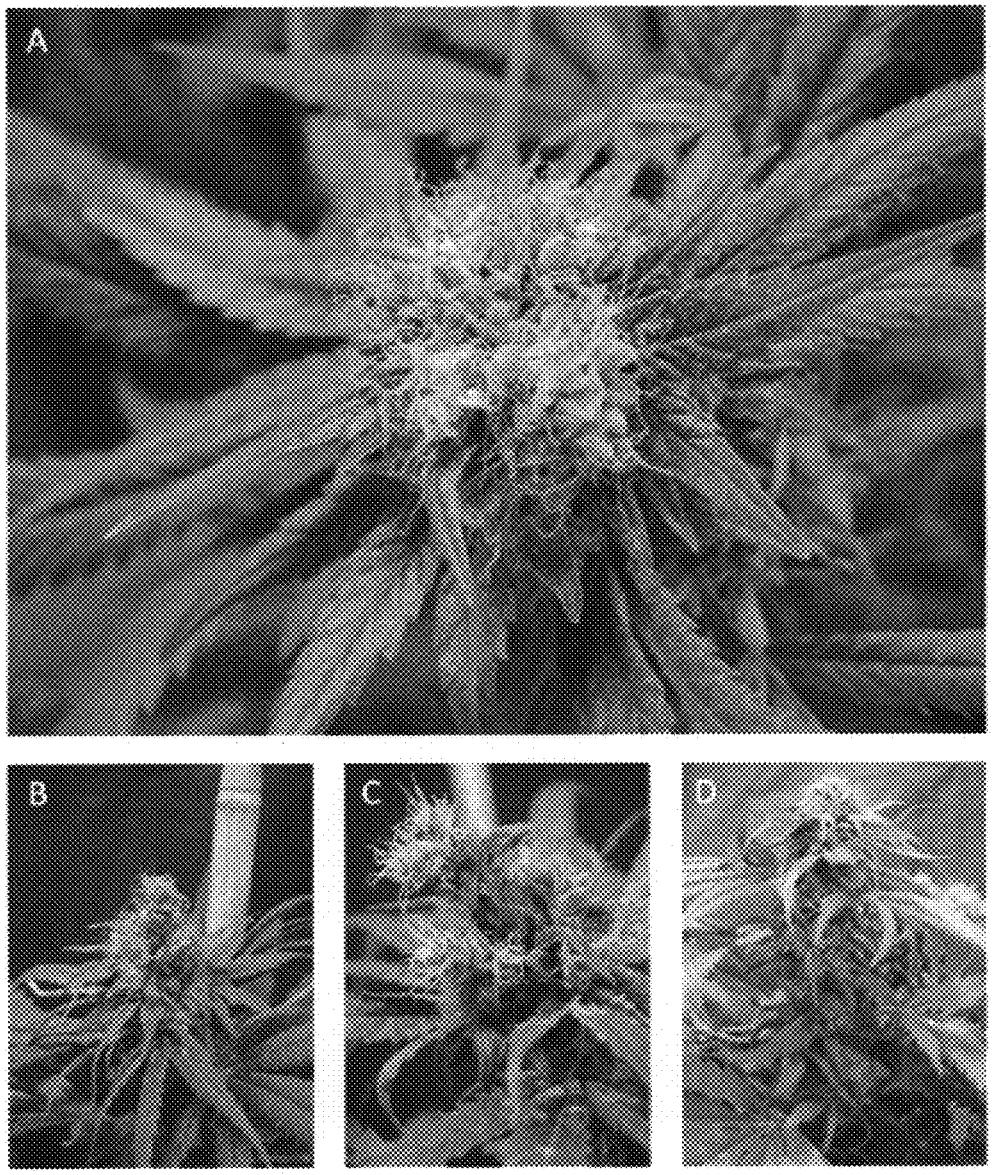
FIG. 4: 'PG 1 19 0125 0002' indoor grown growth pattern during flowering. A and D are a single plant representing the most common flower structure observed. B and C and individual flowers showing less common but observed flower structure phenotypes. Plants were photographed 1-3 days prior to harvest.
Figure 5:
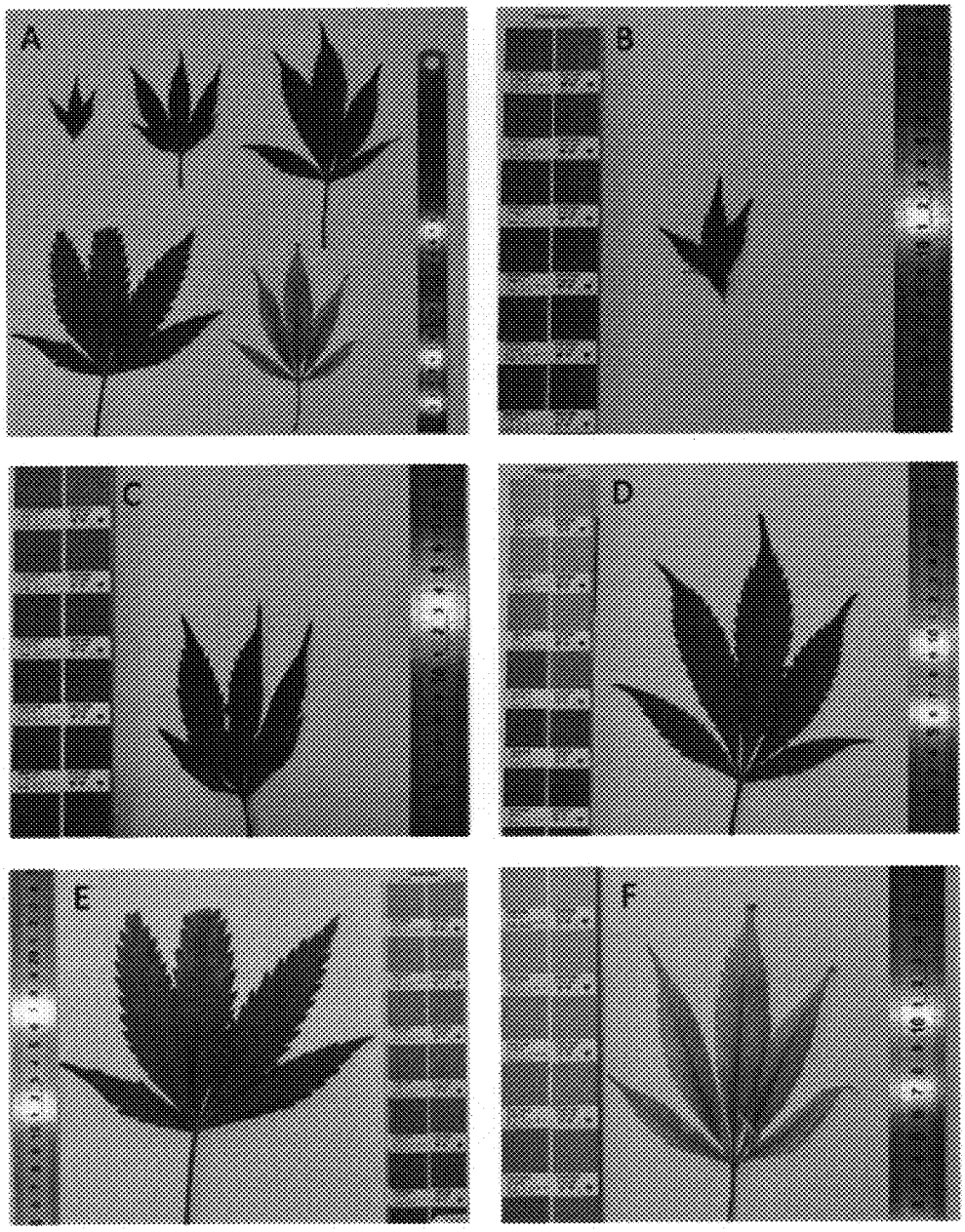
FIG. 5: 'PG 1 19 0125 0002' leaves emerge a very dark green and lighten towards yellow during development. (A) Five leaves throughout indoor grown development. (B) Leaf 3-5 days after emergence. (C-E) Leaves through development but before flower maturation. (F) Senescent leaf after flower maturation. Photos include ruler measures with cm markings and appropriate Pantone swatch for color comparison.
Figure 6:
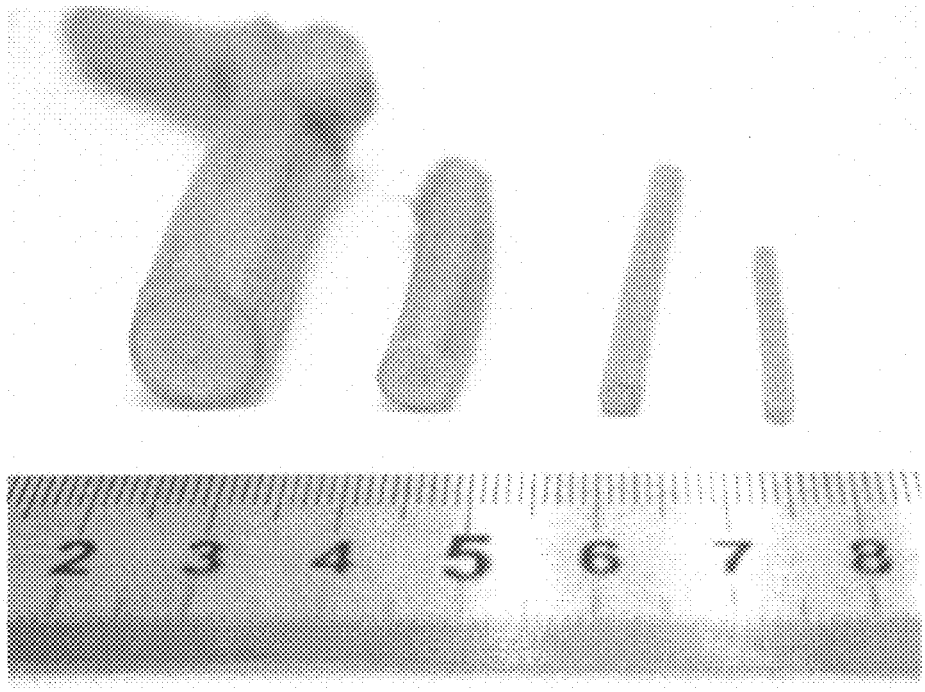
FIG. 6: 'PG 1 19 0125 0002' stem sections from a single plant illustrating a filled/solid stem and not a hollow one common in other varieties. (Left) Section below the first node on the primary stem, closest to soil level. (Center left) Primary branch. (Center right and right) Flower bearing terminal branches. Ruler for scale with cm markings.
Figure 7:
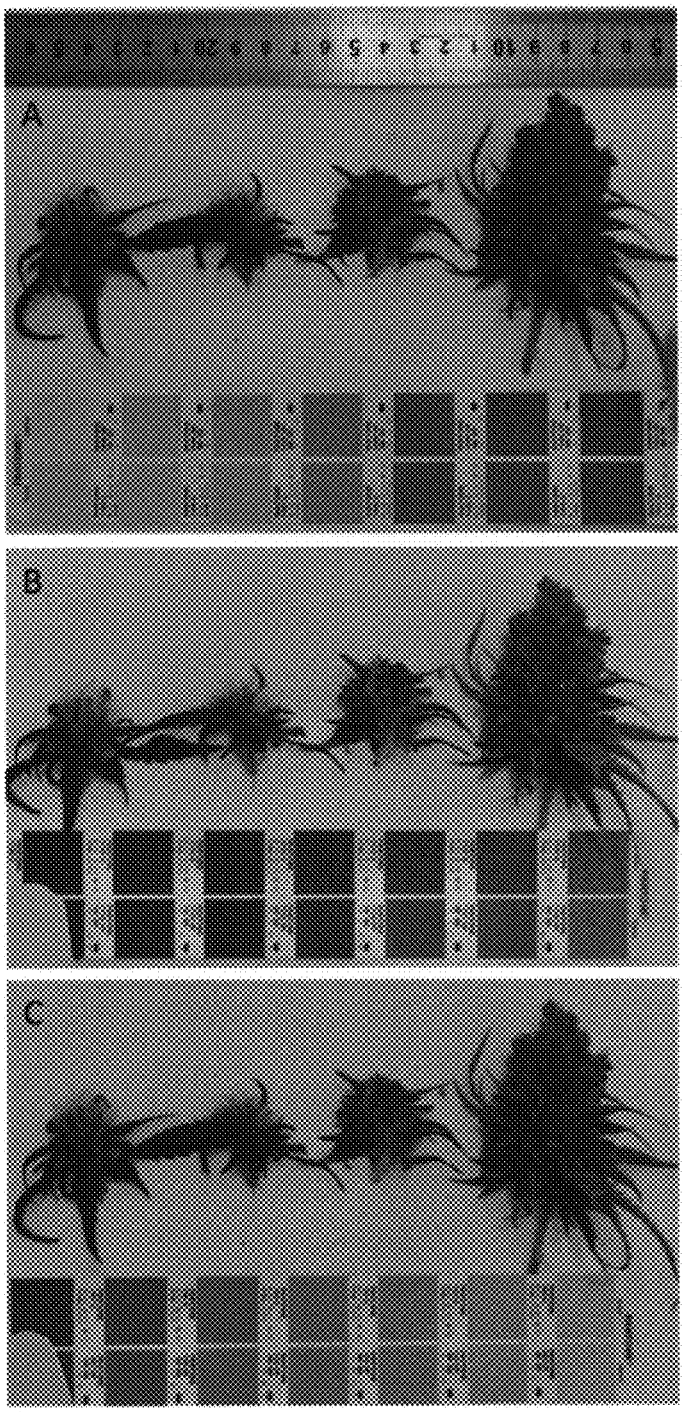
FIG. 7: Four representative flowers of indoor grown 'PG 1 19 0125 0002' illustrating the typical development of the stigma coloration which begins a very light green and turn a deep red-brown during maturation. (A-C) Identical flowers photographed with varied Pantone swatches for color comparison. Ruler for scale with cm markings.
Figure 8:
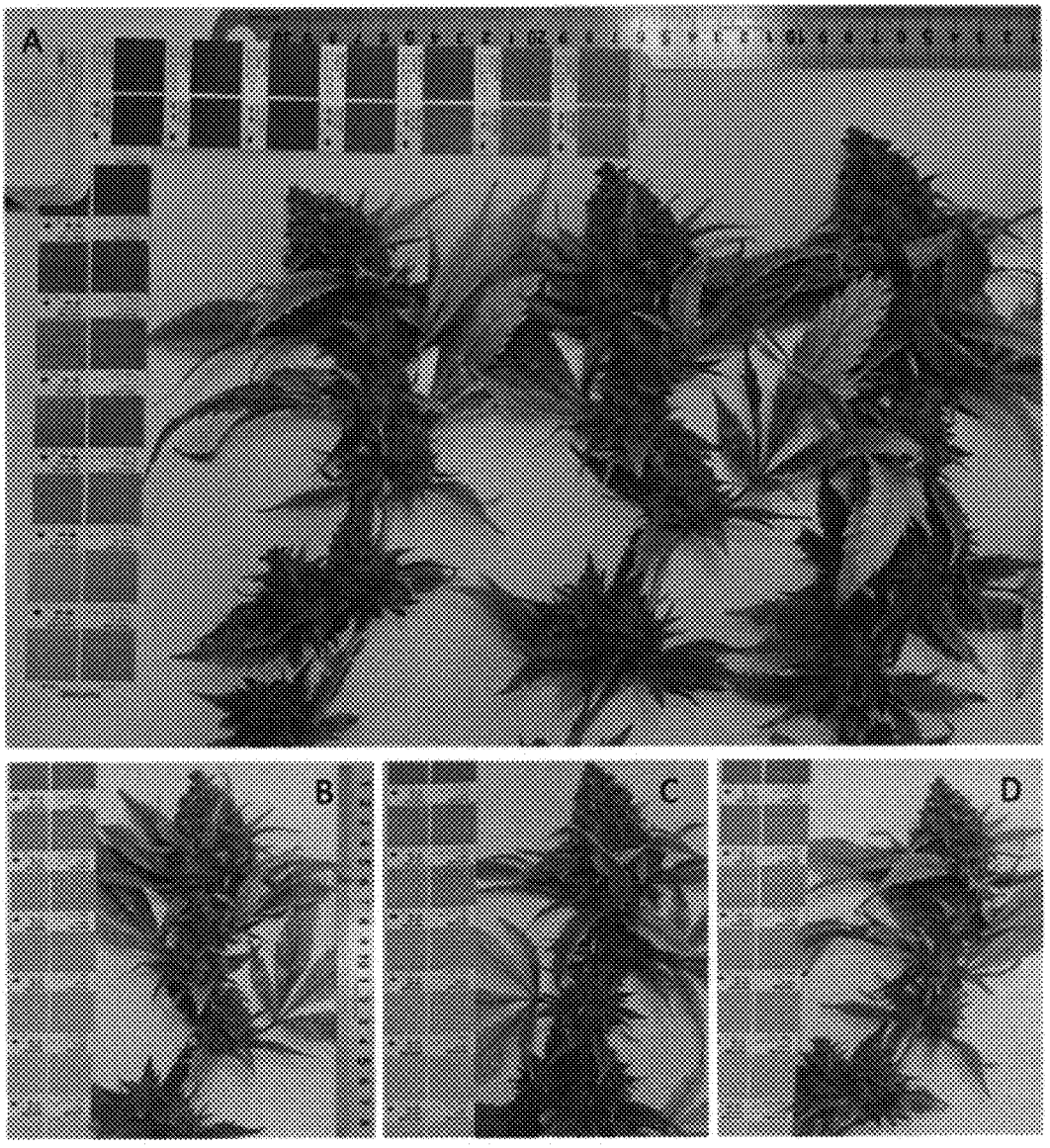
FIG. 8: Three representative branches of an individual indoor grown 'PG 1 19 0125 0002' prior to harvest. (A) All three branches photographed together. (B-D) The same branches photographed individually. Branches are photographed with varied Pantone swatches for color comparison and with a ruler with cm markings for scale.
Figure 9:
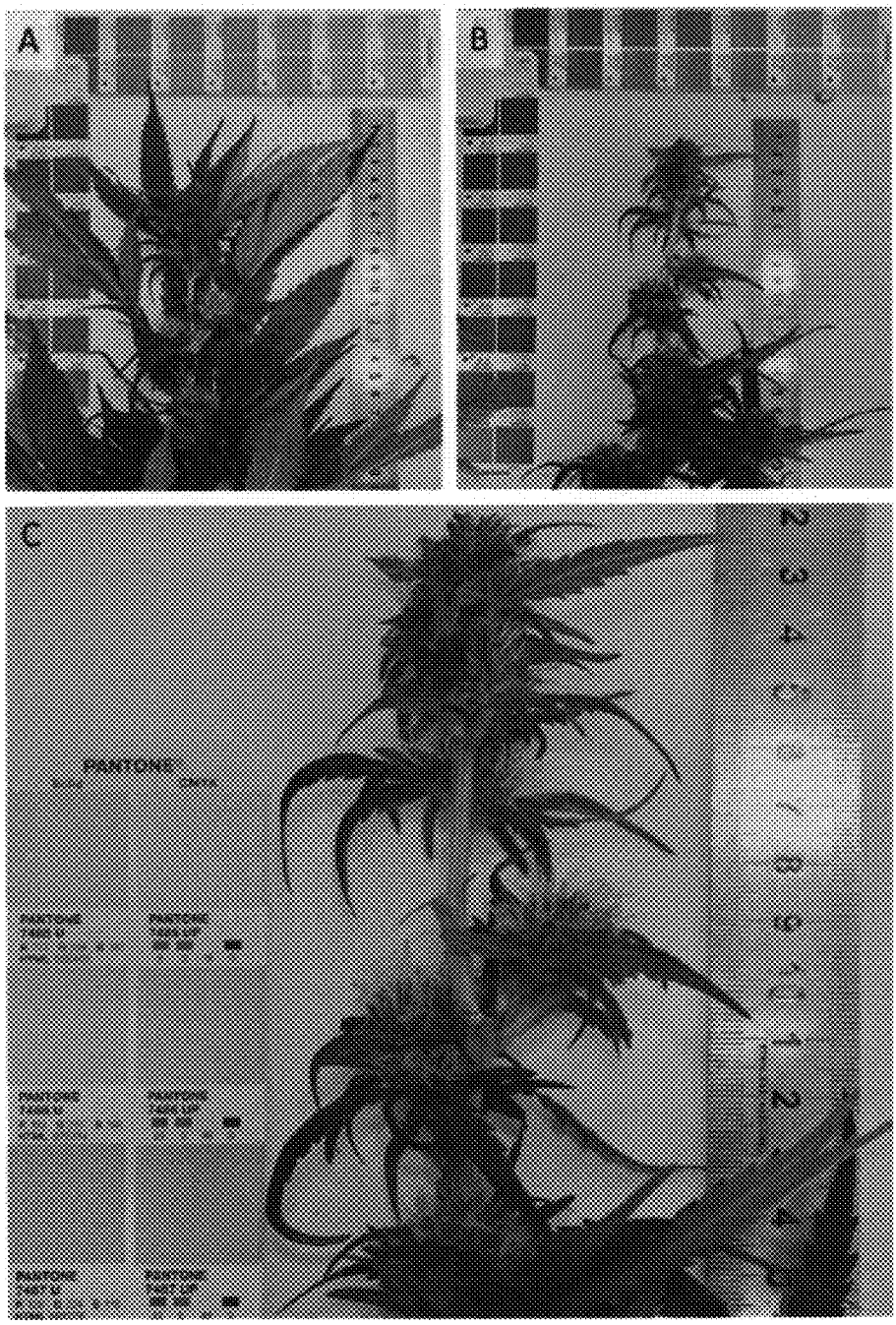
FIG. 9: A single branch of indoor grown 'PG 1 19 0125 0002' showing immature flowers. (A) The branch with leaves intact showing the ventral red coloration of the petioles. (B) The same branch manually defoliated around the apical flowers. (C) A closer image to illustrate the length and color of the stigma at this mid flower developmental stage. Branches are photographed with varied Pantone swatches for color comparison and with a ruler with cm markings for scale.
Figure 10:
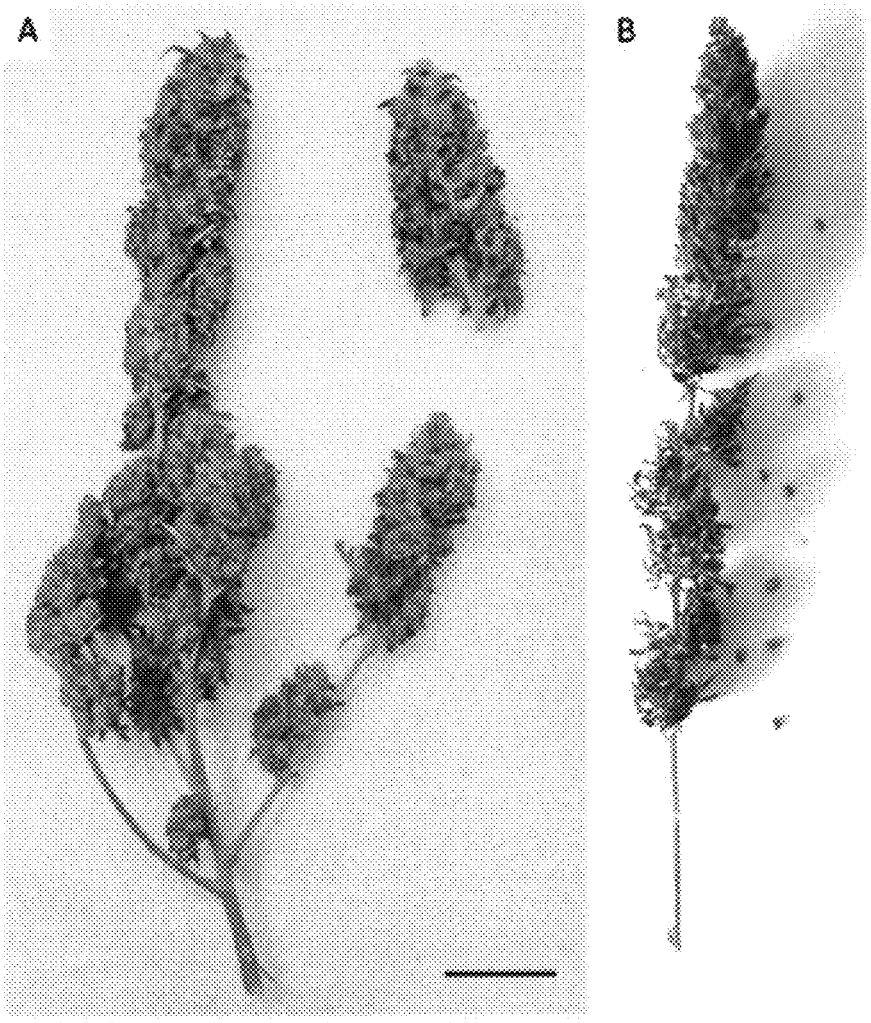
FIG. 10: (A) Machine trimmed indoor grown 'PG 1 19 0125 0002' flower harvested at 6.5 weeks after flower initiation. Black bar=5 cm. (B) A dried flower of Santhica 27. Clear differences can be observed in the flower density between the two can be seen. Flower density is a component of flower mass and, therefore, cannabinoid production per flower and per plant.
Figure 11:
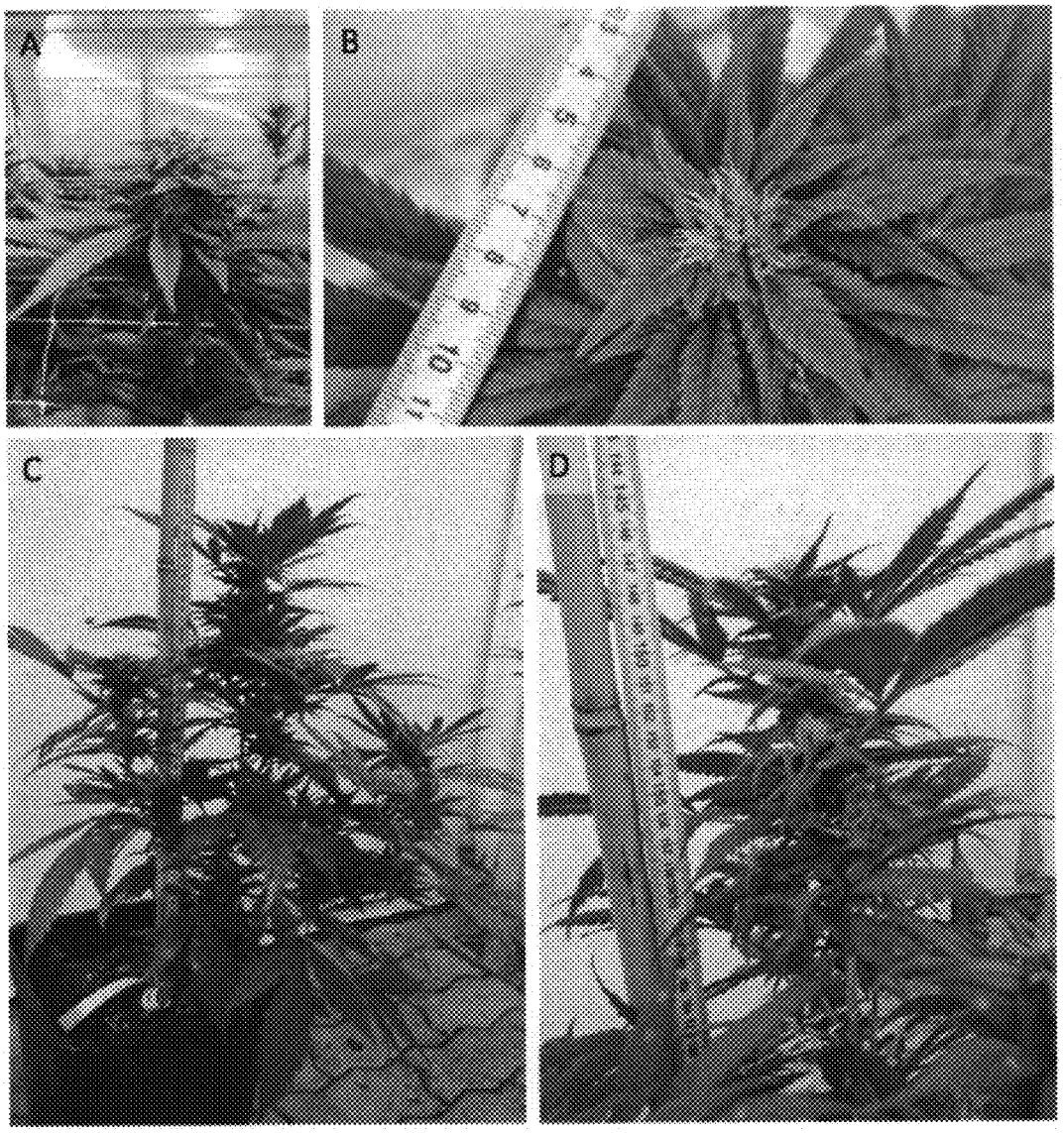
FIG. 11: 'PG 1 19 0125 0002', glasshouse grown, growth pattern during flowering. (A) Side view of a 'PG 1 19 0125 0002' flower 10 days prior to harvest. (B-D) An individual plant photographed early in floral development to show the (B) apical flower, (C) a side view of the whole plant, (D) a view of the apical inflorescence. Ruler for scale with cm markings.
Figure 12:
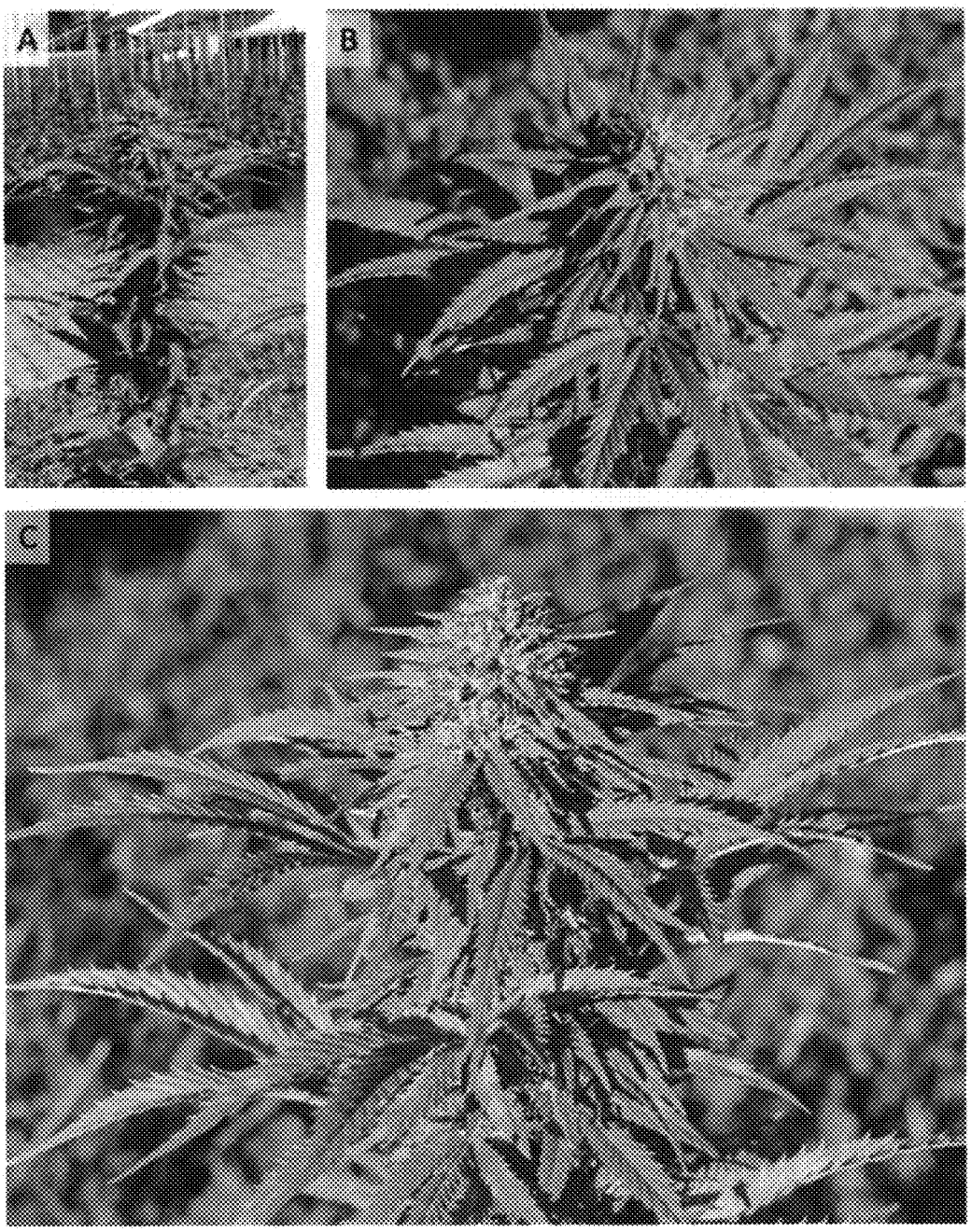
FIG. 12: 'PG 1 19 0125 0002' growth pattern during flowering while grown outdoors near Möhlin, Switzerland. (A) Side view of the apical inflorescence 14 days prior to harvest. (B) A closer image of the apical flower. (C) A side view of the apical inflorescence visualizing the dense trichomes on the flowers.
Figure 13A:
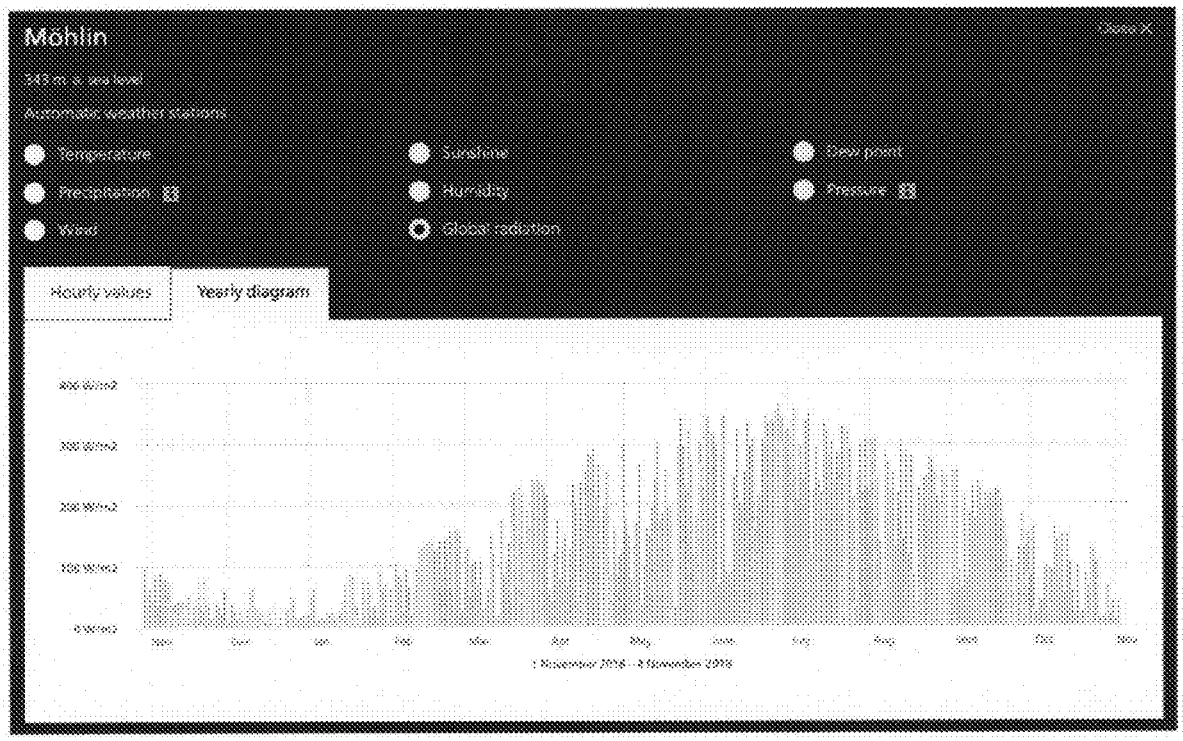
FIGS. 13A-C.
Figure 13B:
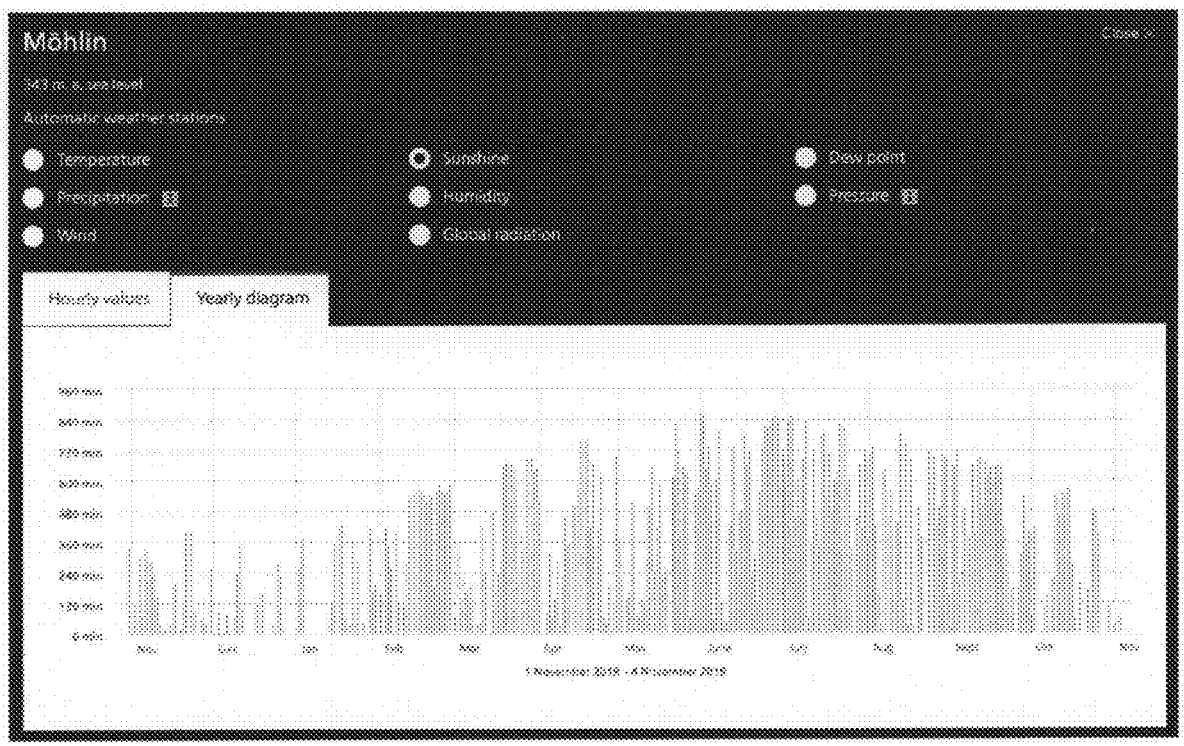
Figure 13C:
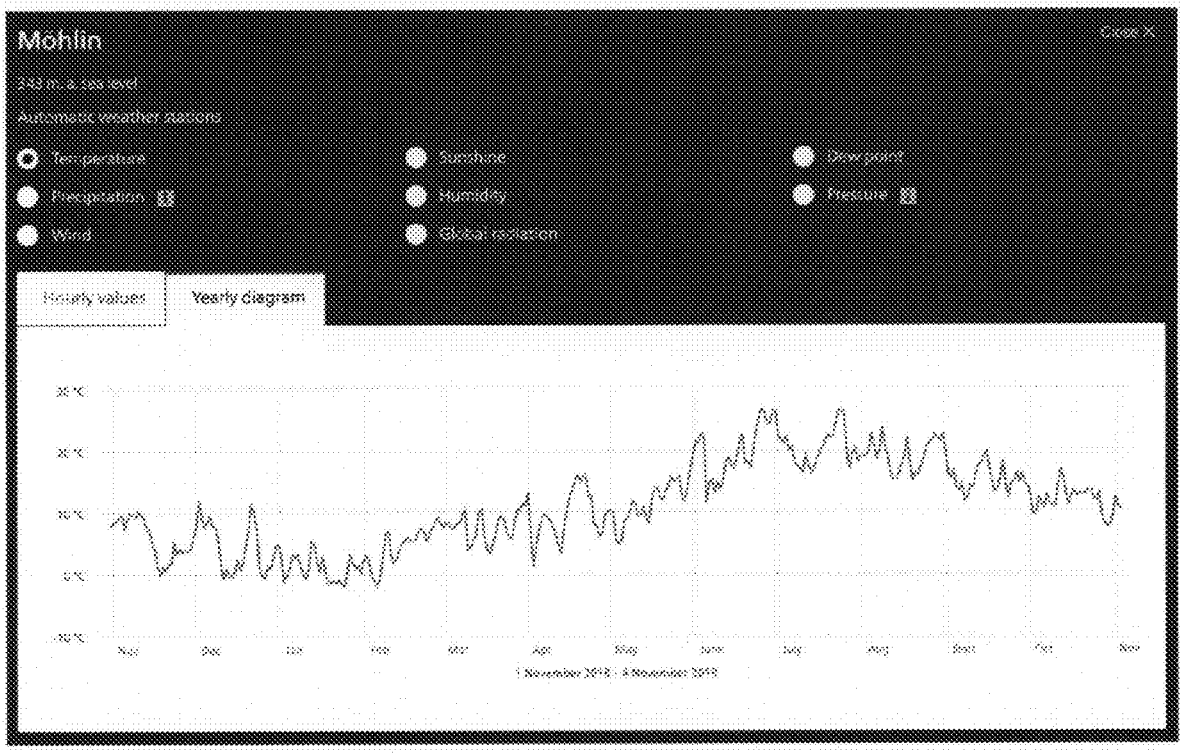
Figure 14:
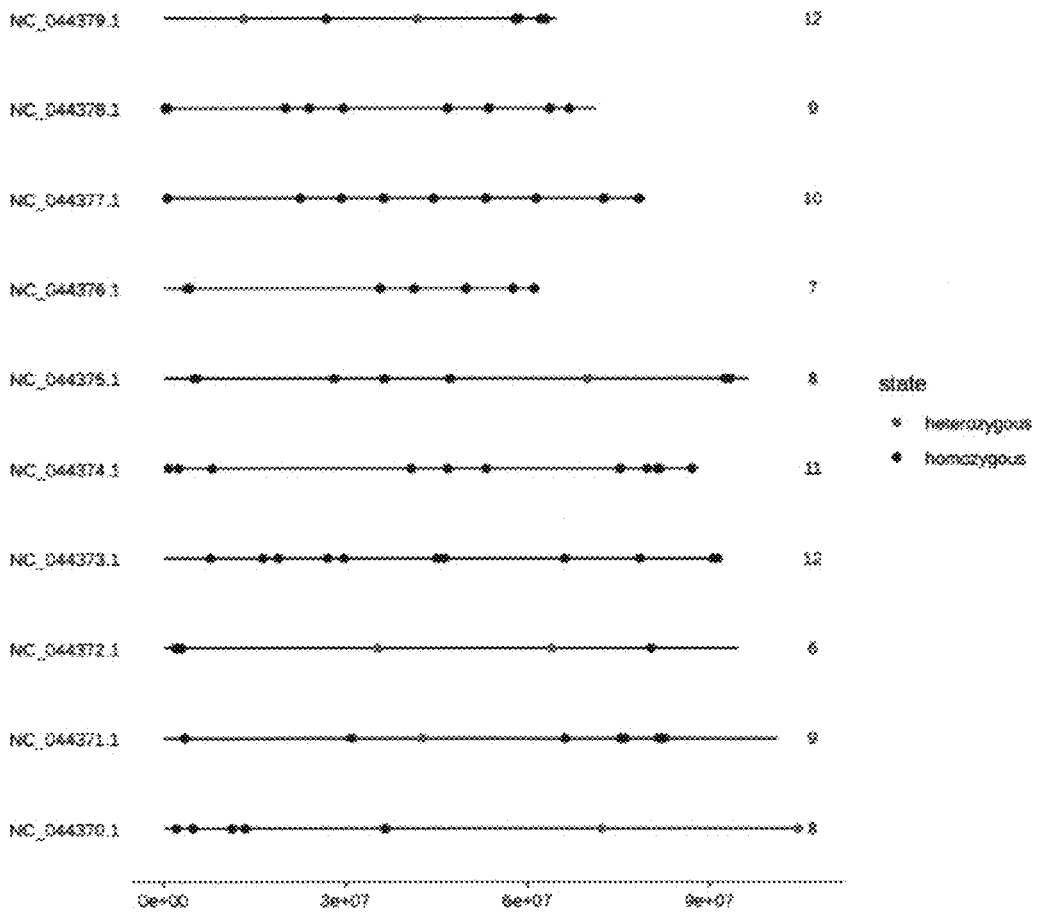
FIG. 14: A graphical representation of the single nucleotide polymorphisms (SNP) and haplotypes (HAPs) contained within the genome of 'PG 1 19 0125 0002' when compared to the publicly available reference genome of cs10 (Assembly: GCF_900626175.1) and shown in Table 2. The chromosomal reference sequence of cs10 is shown on the left and the approximate nucleotide position of the cs10 reference sequence is shown below. Homo- and heterozygous sequence variants are indicated as black and red dots, respectively.

'PG 1 19 0125 0002' was grown in Zeiningen, Switzerland and observations were made in the field, in nursery glasshouses as well as in climate controlled indoor growth facilities. Observed phenotypes may vary in different environmental conditions.

Plants used for the botanical description of the plant are annual, herbaceous, upright, tap-rooted plants. They are *Cannabis* hybrid species and the particular variety described herein is designated the name 'PG 1 19 0125 0002'.

Throughout this specification, color names beginning with a small letter signify that the name of that color, as used in common speech is aptly descriptive. Color number descriptions were obtained using the Pantone Plus Series Color Bridge (ISBN: 978 1-590651-59-9).

'PG 1 19 0125 0002' is a cross between multiple pollen donors and several pollen acceptors of both hemp-type and high CBD-type *Cannabis* plants. The initial cross was made during April 2018. The resultant F1 seeds were grown, cloned, and the clones used for crossing i.e. selfed. The F2 seed was grown, and from this population 'PG 1 19 0125 0002' was selected. The selection criteria were based on the following characteristics: Maximal CBG content and minimal THC and CBD content in the mature flower, flower density, and a highly branched plant structure. The variety was first vegetatively reproduced on the 12$^{th}$ of April 2019 and the resultant plants screened for high total CBG production and selected based on production relevant phenotypes. The progeny with the most stable desirable chemotype was assigned the name, 'PG 1 19 0125 0002'. 'PG 1 19 0125 0002' continues to be vegetatively reproduced by cloning in Zeiningen, Switzerland.

When 'PG 1 19 0125 0002' is compared to the *Cannabis* variety 'Santhica 27' (UPOV grant number: 1004490), some similarities and many distinct characteristics become apparent. Both 'PG 1 19 0125 0002' and 'Santhica 27' present with CBG as the dominant cannabinoid, with extremely low THC and CBD levels. 'PG 1 19 0125 0002', however, displays a up to six times more CBG in dried flowers than 'Santhica 27'. Moreover, the 'PG 1 19 0125 0002' flowers develop into a significantly denser inflorescence. Morphologically, 'PG 1 19 0125 0002' is short and highly branched with large flowers on each branch, reaching a maximum height of approximately 1 meter, whereas 'Santhica 27' is tall and mostly unbranched with a dominant apical inflorescence, reaching a height of up to 2.5 meters. The characteristics listed above, including branching, flower density, and significantly more CBG per unit mass, results in the 'PG 1 19 0125 0002' variety presenting with a substantially higher harvest index than 'Santhica 27' with respect to CBG production.

'PG_1_Pre-19_0125_0004' is a close relative of 'PG 1 19 0125 0002' from the Pure *Cannabis* Research breeding program and displays an almost identical growth pattern and general phenotype. A clear difference between the two varieties can be seen in their cannabinoid profiles (See Table 1 above). The cannabinoid profile of the 'PG_1_Pre-19_0125_0004' flower is clearly CBD-dominant with significant THCA accumulation.

Below is a detailed description of the new variety 'PG 1 19 0125 0002' (See also Table 3, above). Unless otherwise stated measurements were taken from plants grown indoors at various stages of development up to 11 weeks after cloning.

The 'PG 1 19 0125 0002' cultivar is a mixed hybrid of the *Cannabis* sp. It is naturally obtained and not the result of any genetic modification techniques.

Plant:

*Plant life form and growth habit*.—An annual herbaceous plant described as broad, upright, tap-rooted.

*Plant propagation*.—Asexually propagated by cutting and cloning methods.

*Propagation ease*.—'PG 1 19 0125 0002' is easy to propagate.

*Height*.—Approximately 50 cm to 100 cm.

*Width*.—Approximately 30 cm to 50 cm.

*Plant vigor*.—Medium — 'PG 1 19 0125 0002' bears large flowers without the requirement for excessive growth.

*Time to harvest*.—From time of cloning the plant will take approximately 8 weeks to be harvest-ready.

*Resistance to pathogens*.—Partial resistance. It is known to be moderately susceptible to *Botrytis*.

*Genetic modification*.—It is naturally obtained and not the result of any genetic modification techniques.

*Conditions of flowering*.—'PG 1 19 0125 0002' flowers once the daylight period is reduced to 12 hours daylight.

*Hardiness*.—'PG 1 19 0125 0002' easily tolerates temperatures up to 26° C.

*Breaking action*.—This variety has a sturdy main stem with a "pithy" center. It is not highly flexible, but resistant to breaking. The flexible side branches are highly resistant to breaking.

*Rooting behavior*.—When propagated according to PureGene's standard operating procedures, it roots vigorously at a rate of 98% within 7-10 days.

Leaf:

*Arrangement*.—Alternating.

*Shape*.—Palmately compound.

*Structure*.—Leaflet blades are very elongated, elliptical, lanceolate with acute tips and bases.

*Margins*.—Serrated with teeth pointing toward the leaflet tips.

*Hairs*.—Extremely fine sericreous hairs pointing toward the leaf tips.

*Mature leaf measurements*.—Leaf length with petiole: Approximately 23 cm. Petiole length: Approximately 5 cm. Stipule length and shape: Approximately 0.4 cm to 1.5 cm linear with acute tip. Leaflet number: About 3 to 9. Middle leaflet length: width: Approximately 14:3. Teeth on middle leaflet: Approximately 15 to 30. Width of central leaflets: Approximately 30 mm to 35 mm for plants grown in indoors conditions.

*Leaflet apex shape*.—Acuminate acute.

*Adaxial leaf trichomes* (*upper and lower surface*).—capitate stalked, capitate sessile and cystolithic trichomes.

*Abaxial leaf trichomes* (*upper and lower surface*).—Capitate stalked, capitate sessile and cystolithic trichomes.

*Abaxial petiole color range*.—About Pantone 380-383 UP with gradual anthocyanin coloration of 7624 U and UP during flowering.

*Adaxial petiole color range*.—About Pantone 382-385 UP with gradual anthocyanin coloration of 7624 U and UP during flowering.

*Stipule color range*.—About Pantone 382-384 UP.

*Leaf color of the adaxial surface*.—About Pantone 347-349 UP, 7734-7745 UP (leaf color changes from very dark green to the yellow spectrum with age).

*Leaf color of the abaxial surface*.—Pantone 345-347 UP-7730 UP) The lower surface of the leaf changes from a dark green to light yellow spectrum with age.

*Leaf glossiness*.—Average, becoming more matt at the apical ends as flowers mature.

*Midrib shape*.—Prominent and continuous throughout each leaflet.

*Midrib color*.—The midrib is a dark green, similar in shade to a younger leaf. As the leaf lightens with maturity, the midrib remains a dark green color (Pantone 349 UP).

*Aroma*.—Earthy with citrus and fruit.

Stem:

*Shape*.—The stem is ribbed with a solid center.

*Diameter*.—Approximately 2 cm to 5 cm.

*Color*.—Varying shades of about light green depending on age (Pantone 7488 UP).

*Main stem groove*.—Longitudinally ridged with medium grooves in immature stem, axillary branches, and mature branches proximal to flowering ends. Grooves gradually smooth out on older parts of the stem which, at maturity, are smooth and woody with a solid pith.

*Stem trichomes*.—Capitate sessile glandular trichomes and unicellular non-glandular trichomes. Only unicellular non-glandular trichomes on the older, smooth parts of the stem.

*Stem internode length*.—Short during early vegetative phases elongating as the plant matures. During late vegetative phase the average length of the internodes is medium. The internodes shorten exponentially towards the flowering ends exhibiting as very short directly below the compound inflorescence.

Inflorescence:

*Flowering habit*.—During vegetative phase individual flowers occur at nodes along the stem and branches. Upon flower initiation flowers appear as clusters, or compound inflorescences, as a result of higher order branching and shortened internodes. Terminal inflorescences appear as compressed and dense while more distal inflorescences gradually decrease in size and density with a scattered appearance.

*Proportion of female flowers*.—100%.

*Inflorescence position*.—Above.

*Flower arrangement*.—Individual flowers (bracteoles) on each mature, compound inflorescence are tightly packed, congested, concentrated and crowded, touching and overlapping with stigmas curling over adjacent bracteoles with maturity.

*Number of flowers per plant*.—About 50 to 100.

*Individual flower shape*.—Each individual flower has one ovary enclosed in an urceolate bract with two long filiform stigmas protruding from each ovary and exiting above the bract.

*Compound inflorescence shape*.—Compound inflorescences are ovaloid in shape with bilateral symmetry.

*Flower compound inflorescence diameter*.—The average diameter around the terminal flower compound is 6 cm to 20 cm.

*Pistil length*.—The length from the base of the ovary to the tips of the stigmas is approximately 2 cm to 10 cm.

*Style length*.—There is no discernible style connecting the stigmas to the ovary. The stigma refers to the entire length from the upper curve of the ovary to the tip of the stigmas.

*Bract shape and color*.—Urceolate and about dark green (Pantone 7731 UP).

*Stigma shape*.—Extremely elongated, elliptical, filiform and visible as hair-like filaments on the surface of flower compounds.

*Stigma length (from the upper surface of the ovary to the tip of the stigma)*.—Approximately 2 mm to 10 mm.

*Stigma color*.—The color changes from a about white/light green (Pantone 7485 UP) to about deep red-brown (Pantone 167 UP) as the flowers mature.

*Trichome color*.—Initially clear becoming cloudy/milky white and then developing an amber color about Pantone 475 UP at 5 weeks post flowering.

*Trichome shape*.—All flowering parts including the bracteoles and bracts are covered in capitate stalked, capitate sessile and bulbous glandular trichomes.

*Terminal bud shape*.—Acute ovoid.

*Terminal bud color*.—At maturity the terminal bud appears about dark green (Pantone 7731 UP) partially covered by deep red-brown (Pantone 167 UP) hair-like stigmas.

*Male flower characteristics*.—'PG 1 19 0125 0002' clones are propagated only as females and the male flower characteristics are not relevant to the physical botanical characterization of this variety.

*Cannabinoid contents*.—$CBG_{max}$—9.44%, $CBD_{max}$—0.21%, $THC_{max}$—0.13%.

*Flower fragrance*.—Earthy with citrus notes in line with the presence of limonene in the terpene profile.

*Flower shipping quality*.—It is a dense appealing flower when trimmed, cured and packaged according to quality guidelines. Dry flowers are of high quality and suitable as a direct-to-consumer commodity.

*Flower storage life*.—A minimum of 1 year if packaged according to quality guidelines.

*Flower indoor productivity*.—Approximately 0.9 g/watts.

*Flowering season*.—In Zeiningen flowering is initiated around 11 August when the daylength reduces to 14.25 h. This may be different at different latitudes.

Seed:

*Shape*.—Solitary, ovoid and slightly compressed.

*Size*.—Lateral: Approximately 3 mm. Longitudinal: Approximately 4 mm.

*Color of the testa*.—Variable but generally a mottled brown-gray color ranging from About Pantone 4515 U at the light scale to 7532 UP at the dark scale with very dark brown about Pantone 7533 UP to black speckling.

What is claimed is:

1. A new and distinct variety of *Cannabis* plant named 'PG 1 19 0125 0002', substantially as illustrated and described herein.

* * * * *